United States Patent
Remmers et al.

(10) Patent No.: US 6,286,508 B1
(45) Date of Patent: *Sep. 11, 2001

(54) AUTO CPAP SYSTEM PROFILE INFORMATION

(75) Inventors: John Edward Remmers; Thomas Richard Feroah, both of Calgary (CA)

(73) Assignee: University Technologies International, Inc., Calgary (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/158,345

(22) Filed: Sep. 21, 1998

Related U.S. Application Data

(63) Continuation of application No. 08/842,981, filed on Apr. 25, 1997, now abandoned, which is a continuation of application No. 08/093,131, filed on Jan. 29, 1993, now Pat. No. 5,645,053, which is a continuation of application No. 07/868,199, filed on Apr. 14, 1992, now abandoned, which is a continuation of application No. 07/791,733, filed on Nov. 14, 1991, now abandoned.

(51) Int. Cl.[7] .................................................. A61M 16/00
(52) U.S. Cl. ................... 128/204.18; 128/204.21; 128/204.23
(58) Field of Search ................... 128/204.18, 204.21, 128/204.23

(56) References Cited

U.S. PATENT DOCUMENTS

| | | | |
|---|---|---|---|
| 5,117,819 | * 6/1992 | Servidio et al. | 128/204.21 |
| 5,148,802 | * 9/1992 | Sanders et al. | 128/204.23 |
| 5,199,424 | * 4/1993 | Sullivan et al. | 128/204.23 |
| 5,239,995 | * 8/1993 | Estes et al. | 128/204.21 |
| 5,245,995 | * 9/1993 | Sullivan et al. | 128/204.23 |
| 5,645,053 | * 7/1997 | Remmers et al. | 128/204.21 |

* cited by examiner

Primary Examiner—Aaron J. Lewis
(74) Attorney, Agent, or Firm—Burns, Doane, Swecker & Mathis LLP

(57) ABSTRACT

The present invention relates to systems and methods for automatically and continuously regulating the level of nasal pressure to an optimal value during OSA treatment. OSA therapy is implemented by a device which automatically re-evaluates an applied pressure and continually searches for a minimum pressure required to adequately distend a patient's pharyngeal airway. For example, this optimal level varies with body position and stage of sleep throughout the night. In addition, this level varies depending upon the patient's body weight and whether or not alcohol or sleeping medicine has been ingested.

18 Claims, 8 Drawing Sheets

AUTO CPAP SYSTEM PROFILE INFORMATION

RELATED APPLICATION

This application is a continuation, of application Ser. No. 08/842,981 filed on Apr. 25, 1997, now abandoned which is a continuation of Ser. No. 08/093,131 filed on Jan. 29, 1993, now U.S. Pat. No. 5,645,053 issued Jul. 8, 1997 which is a continuation of Ser. No. 07/868,199 filed on Apr. 14, 1992, now abandoned, which is a continuation of application Ser. No. 07/791,733 filed Nov. 14, 1991, now abandoned.

BACKGROUND OF THE INVENTION

1. Field of the Invention

The present invention relates generally to systems and methods for treating sleep disorders. More particularly, the invention relates to systems and methods for treating obstructive sleep apnea using an adaptive control system for applying air pressure to the nasal airway.

2. State of the Art

Obstructive sleep apnea (OSA) is a newly recognized disease that victimizes 15% of adult males. The disorder arises during sleep when the victim undergoes repeated cessation of breathing. This cessation results from an obstruction of the throat air passage (pharynx) due to a collapse of the throat air passage. Repeated cessation of breathing reduces blood oxygen and disturbs sleep. Reduction in blood oxygen can cause heart attacks and strokes. Sleep disturbances can produce excessive daytime sleepiness, a leading cause of auto accidents.

Medical research over the past decade has provided only one effective and practical approach to OSA therapy, known as nasal continuous positive airway pressure (CPAP). In this therapeutic approach, a patient's nose is covered with a mask that forms a pressure seal with the surrounding face. While the patient sleeps, the mask is pressurized to a level that distends the collapsible throat air passage, thereby preventing obstruction.

This therapeutic approach provides two significant advantages: it is uniformly effective and it is entirely benign. A major disadvantage of this approach is that the patient must remain overnight in a hospital sleep center to undergo a full night polysomnography study with the pressure mask in place to determine the therapeutic level of pressure. A further disadvantage of this approach is that the pressure delivered to the patient during the polysomnography study is constant and fixed at the prescribed level, even though the patient's requirements may vary throughout the night and from night-to-night.

The overnight study represents a major bottleneck to treating hundreds of thousands of patients with OSA because it typically requires two full night polysomnographic studies for each new patient: one to establish the diagnosis (diagnostic-polysomnogram) and another to establish the aforementioned therapeutically optimal pressure (therapeutic-polysomnogram). The therapeutic polysmnographic study is necessary to determine the minimum level of pressure required to produce a patent pharyngeal airway (i.e., to determine the necessary therapeutic pressure required for properly treating the patient). These studies, performed in a specialized hospital sleep center, allow a specialist to specify the pressure to be used when prescribing nasal CPAP therapy. For this reason, the therapy cannot be prescribed by an internist or general practitioner.

Due to the requirement of two night polysomnographic studies, hospital sleep centers are crowded even though only a small percentage of OSA victims are presently being treated. Further, the significant cost of the overnight polysomnographic study by a hospital sleep center represents a significant obstacle to diagnosing and treating the large population of sleep apneics. The backlog of undiagnosed and untreated OSA patients thus represents a substantial public health problem.

To address the foregoing drawbacks of existing approaches to diagnosis and treatment of OSA, recent commercial technology provides overnight, unattended monitoring of breathing in the patient's home. Such unattended monitoring generally permits the physician to diagnose OSA without requiring a diagnostic overnight study in the hospital sleep center. However, a hospital sleep center is still required for establishing the therapeutically optimal pressure of nasal CPAP in each patient. Accordingly, medical practitioners have been slow to use the new monitoring technology for diagnostic purposes since the patient must, in any case, be referred to a sleep center for a full night therapeutic polysomnographic study.

Accordingly, it would be desirable to render the diagnosis and therapy of OSA more practical, convenient and inexpensive. To achieve this end, a method and system for automatically establishing the desired nasal CPAP pressure is needed. More particularly, a positive airway pressure system is required which will allow a physician, following diagnosis with convenient monitoring technology, to prescribe nasal CPAP without specifying the pressure.

SUMMARY OF INVENTION

The present invention is therefore directed at providing a practical, convenient and cost-effective system for diagnosing and treating OSA. Further, the invention is directed to portable systems and methods for automatically and continuously regulating the level of nasal pressure to an optimal value during OSA treatment. OSA therapy is implemented by automatically applying an appropriate pressure level to a patient. The applied pressure is continuously re-evaluated and optimized. This optimal level varies with body position and stage of sleep throughout the night. In addition, the required pressure varies depending upon the patient's body weight and whether or not any deleterious substances, such as alcohol or sleeping medicine, have been ingested.

Thus, the present invention relates to systems and methods for adaptively providing continuous positive airway pressure to an upper airway system by detecting airflow data in the upper airway system at predetermined increments of time; averaging said airflow data over a second period of time which includes a plurality of said predetermined time increments; determining non-respiratory airflow using said averaged data; identifying periods of inspiration and expiration using said non-respiratory airflow data; extracting information or features from said airflow data; and continuously adjusting pressure in said upper airway system.

In a preferred embodiment, a portable adaptive control system is provided which continually searches for the optimal minimum pressure required to adequately distend a patient's nasal pharyngeal airway. By rendering the system portable, a large percentage of OSA victims can be cost-effectively treated in their homes, thus reducing the overcrowding in expensive hospital sleep centers. Optimal minimum pressure is used because higher pressures increase the likelihood of side effects (e.g., daytime rhinitis), and reduce the likelihood of patient compliance. A patient's compliance in regularly using the system is a significant concern inasmuch as the system is a portable device used at the patient's home without the supervision of a hospital sleep center specialist.

To address the need for a practical device which will further enhance patient compliance, transducers must not be placed on or in the patient's body. Rather, all information used for automatic pressure adjustments is derived by continuously measuring airflow from the pressure generating source (blower) to the nasal mask. Airflow is measured quantitatively by a pneumotachograph interposed between the pressure generating source and the mask. This continuous measure of airflow provides a feedback signal for the adaptive control system to maintain a desired level of output pressure.

BRIEF DESCRIPTION OF THE DRAWINGS

Other objects and advantages of the present invention will become more apparent from the following detailed description of preferred embodiments when read in conjunction with the accompanying drawings, wherein like elements have been designated by like numerals and wherein.

DETAILED DESCRIPTION OF THE PREFERRED EMBODIMENTS

1. Overview

In accordance with a preferred embodiment, the present invention relates to an auto-CPAP system for adaptively providing continuous positive airway pressure in an upper airway system (e.g., pharyngeal airway of a patient). The auto-CPAP system performs detection, analysis, and decision-making functions.

2. System Description

Figure 1A:
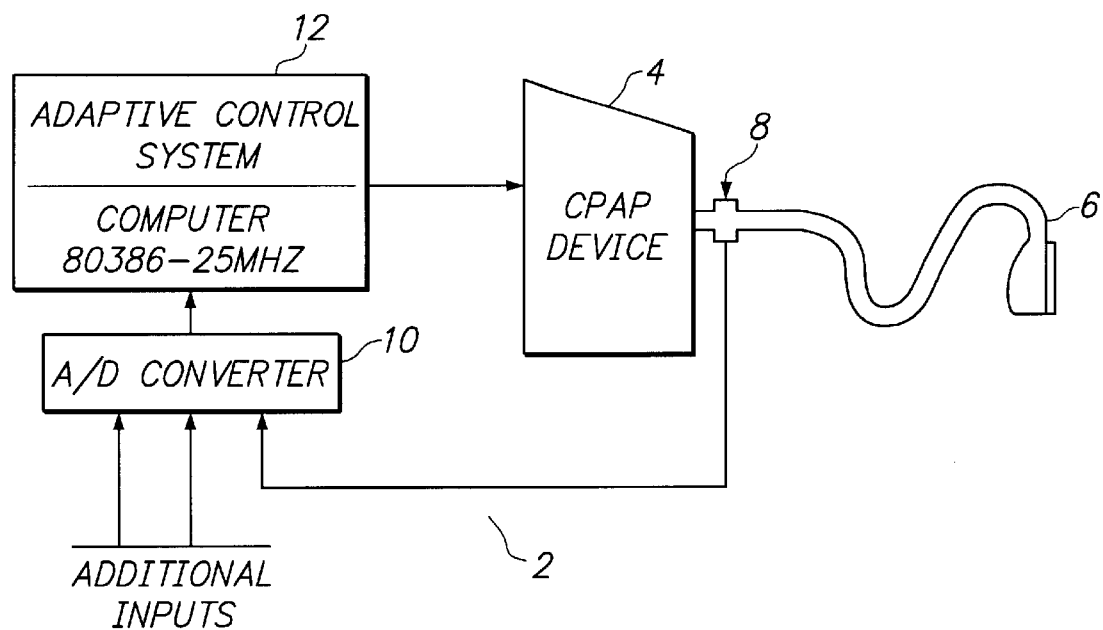
FIG. 1a shows an exemplary embodiment of an auto-CPAP system with an adaptive control feature.

As illustrated in FIG. 1a, an exemplary system is generally labelled 2 and includes means for detecting airflow from the CPAP device. The means of detecting airflow is shown in FIG. 1a to include a pneumotach 8 for measuring instantaneous airflow. The pneumotach includes a pressure transducer and an amplifier for generating an electric signal proportional to airflow.

Airflow is used to assess the respiratory and dynamic mechanical characteristics of a patient's pharyngeal airway (PA) during sleep and to adjust the therapeutic CPAP pressure as required. Total airflow is the sum of non-respiratory and respiratory airflow. The non-respiratory airflow corresponds to a bias flow plus system leaks.

Respiratory airflow typically corresponds to patient breathing and has two sequential, tidal components: one caused by inhalation and another caused by exhalation. This tidal airflow is phasic and therefore allows the onset of inspiration and the onset of expiration to be identified. The onset of inspiration corresponds to the time at which total airflow begins to exceed non-respiratory airflow. The onset of expiration corresponds to the instant when total airflow is less than the non-respiratory value.

Using the non-respiratory airflow, airflow peaks and mean inspiratory airflow can be determined. Because the onset and termination of inspiration are identifiable, parameters related to the shape of a time profile of inspiratory flow can also be determined. In a preferred embodiment, a degree of roundness and flatness of the inspiratory profile are determined as will be described later.

The measurement of airflow and subsequent determination of an inspiratory airflow profile are used to control CPAP in accordance with the present invention. When the level of nasal CPAP that produces the maximal distention with the minimum pressure is abruptly reduced in sleeping patients suffering from OSA, the pharynx is observed to collapse and the pharyngeal resistance increases accordingly. These changes in upper airway resistance induce changes in peak inspiratory airflow and profile shape with little change in airway pressure below the obstruction. Accordingly, changes in airflow resistance can be inferred from changes in the inspiratory airflow.

Further progressive reductions in nasal pressure lead to progressive collapse of the pharyngeal airway which severely reduces inspiratory airflow and causes flow limitations (i.e., increased airflow resistance). As described herein, a flow limitation is a situation where airflow rate is constant and independent of driving pressures. Similarly, progressive increases in nasal pressure lead to smaller decrements in airflow resistance as the pharynx widens and reaches the limits of its distensibility. The collapsible behavior of the pharyngeal airway in response to progressive pressure changes provides a framework for determining an optimal therapeutic CPAP in accordance with the present invention.

Accordingly, a preferred embodiment includes means for generating pressure in the upper airway system in response to detected airflow. This pressure is adaptively adjusted to apply an optimal therapeutic nasal pressure. As illustrated in the exemplary FIG. 1a embodiment, a pressure generating means is represented generally as a CPAP device. The FIG. 1a pressure generating means includes a known, electronically controllable pressure generating device 4, such as the commercially available "Tranquillity Plus" manufactured by Healthdyne Technologies.

The pressure generating device is a computer controlled pressure generator which supplies a commanded pressure to the pharyngeal airway of a patient via a nasal mask 6 worn by the patient. Because the nose mask used has an exhaust port, a bias flow is present which increases at increasing pressure. This bias flow constitutes a portion of the non-respiratory airflow as mentioned previously.

Further, the FIG. 1a embodiment includes means for adaptively controlling the pressure generating means in response to the airflow detecting means to automatically provide optimal CPAP. Such a feature is generally illustrated in FIG. 1a as an A/D converter 10 and an adaptive control system 12. The adaptive control system 10 is shown as a computer (e.g., an IBM 80386 compatible) and interface which communicates a desired pressure to the CPAP device.

Figure 1B:
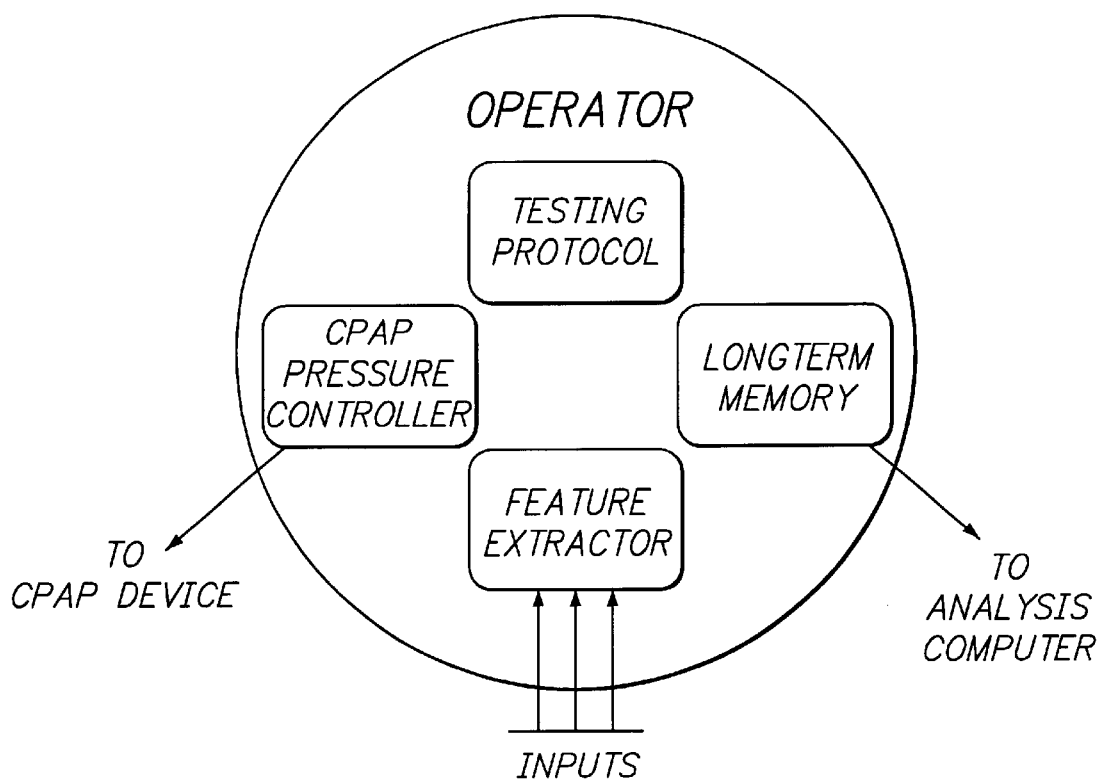
FIG. 1b shows a conceptual diagram illustrating an operator of the adaptive control system.

During a testing mode of the FIG. 1b auto-CPAP system, the pressure in the pharyngeal airway is changed frequently. Presently the pressure is changed by sending the value of the actual pressure value via a serial port to an interface box of the adaptive control system which includes a Z-80 based microcomputer board (e.g., Micromint's BCC52 computer/controller). The interface box reads the pressure and then converts it to a format (e.g., four line parallel input) for the normal remote control input into the pressure generating device.

Generally speaking, the adaptive control system generates an optimal desired (i.e., command) pressure by averaging airflow data over a predetermined period of time, partitioning airflow data into respiratory and non-respiratory components, identifying periods of inspiration and expiration using the non-respiratory component, and extracting information or features from airflow data. Using this information, the adaptive control system identifies a critical pressure ($P_{crit}$) at which a significant obstruction occurs during inspiration. More particularly, $P_{crit}$ corresponds to a lower limit of mask pressure associated with a significant decrease in peak inspiratory airflow and/or significant (i.e., critical) airflow limitation. After determining $P_{crit}$, the adaptive control system identifies an optimum (i.e., minimum) effective CPAP ($P_{opt}$) for eliminating the obstruction during inspiration.

The adaptive control system identifies $P_{crit}$ and decides upon $P_{opt}$ using a series of test perturbations in the mask pressure. Results of the tests are evaluated by examining inspiratory airflow. $P_{opt}$ is continuously updated during testing periods which are initiated throughout the night to account for changes in the patient's sleep stages and sleeping position.

Because a testing period is used to update $P_{opt}$, the adaptive control system also decides when to test the pharyngeal airway, and when to continue or to stop testing. Further, the adaptive control system (1) manages overall operation to optimize its own performance, and (2) monitors potential airflow measurement errors to accurately measure upper airway performance as will be described below.

Airflow changes and airflow profile changes in the upper airway system have been determined to be directly related to intra-pharyngeal pressure. By determining upper and lower limits of pharyngeal resistance from changes in airflow during a testing period, $P_{opt}$ can be determined for any patient at any time. Accordingly, the adaptive control system searches for $P_{opt}$ between a lower airflow limitation ($P_{crit}$) and an upper limit (full distention of the airway).

Operating within these relative limits ensures reliable assessment of the pharyngeal airway and an accurate determination of $P_{opt}$. Because airflow varies widely among patients and, for any particular patient, varies with sleep stage, $P_{opt}$ can not be determined by comparing airflow measurements with ideal or predicted standards.

Generally speaking the computer 10 of FIG. 1a conceptually includes four basic components for performing the aforementioned testing and non-testing control. As shown in FIG. 1b, these four basic components are an operator, a feature extractor, a testing protocol, and longterm memory.

a. Operator

The adaptive control operator is an overseer that has access to information of the feature extractor at all times, decides when and when not to enter the testing protocol, controls the flow of information to and from longterm memory, and maintains optimal performance and reliability. Decisions are made by the operator to ensure that the adaptive control system operates within predetermined operating limits so that accuracy is maintained.

The normal operating limits for the adaptive control system are based on rules of operation. These rules of operation ensure that so called performance indices are within predetermined physiological ranges, and that a respiratory phase threshold detection mechanism system is functioning efficiently. Further, these rules are used by the adaptive control system to make decisions, such as when to exit a testing period or when to return to a testing period.

To ensure operation within predetermined physiological limits, the rules are designed to have the adaptive control system operate whenever there is (1) a low to moderate level of variation in respiratory features, (2) no hypoventilation and (3) no apnea. Further, the rules are designed to have the adaptive control system operate with a threshold detection mechanism that adjusts for leaks in the CPAP-to-patient system. The threshold detection mechanism is used by the feature extractor to determine changes in phase of respiration.

For purposes of the present discussion of preferred embodiments, a high variation in the respiratory features is defined as a variation coefficient value of 0.3 or more for four or more specified features (e.g., time of inspiration ($T_i$), total time of breath ($T_{tot}$), mean inspiratory airflow ($V_m$), peak inspiratory airflow ($V_p$), and Roundness) for a set of 5 or 10 breaths depending on whether it is in a testing or a non-testing mode, respectively; hypoventilation is defined as five (5) consecutive breaths with $V_m$ less than 40 percent of the predicted awake supine $V_m$; and apnea is defined as a 10 seconds duration of no change in respiratory phase as determined by the leak adjusted threshold detection mechanism. The threshold detection mechanism is judged to not be completely adjusted to the actual non-respiratory flow when a significant increase or decrease in the calculated non-respiratory flow (0.03 L/sec) has occurred over a period of five (5) breaths.

Satisfaction of these rules and proper adjustment of the threshold detection mechanism are criteria used by the adaptive controller in deciding whether or not to enter a testing mode. If these rules are not satisfied during a non-testing period, either a subsequent testing period is delayed or the CPAP is adjusted or both. If these rules are not satisfied during a testing period, the testing ceases and there is a return to the previous $P_{opt}$, or to a pressure previously set by an outside source, whatever is higher.

As mentioned above, the operator is an overseer which decides when to enter a testing mode. Decisions made by the adaptive control system (e.g., when to test and when to discontinue testing) are based on dynamic characteristics, or performance indices, of the pharyngeal airway during the non-testing and testing periods. During non-testing and testing periods, the adaptive control system continuously monitors breathing variations, hypoventilation, apnea, and signs that the threshold detection mechanism has not been properly adjusted for leaks.

(1) Non-Testing Mode Periods

The adaptive control system operates in one of two basic modes: a non-testing mode (n-TM) and a testing mode (TM). Throughout the testing and non-testing modes, characteristics of the upper airway are continuously detected and evaluated by the feature extractor. In the non-testing mode (i.e., non-testing period), results generated by the feature extractor are used to determine if and when to delay testing, to optimize rules of operation, and to identify deteriorating changes in airflow.

While in the non-testing mode, the FIG. 1 auto-CPAP system monitors the information from the feature extractor. This information is used to determine the presence of large variations in breathing frequency, hypoventilation, apnea, and signs of unadjusted leaks which would affect the nRV. Testing under these conditions could lead to erroneous results. Therefore entering into the testing mode may be delayed. Hypoventilation may also occur during this period if mask pressure is too low.

(2) Testing Mode Periods

When the adaptive control operator decides to redetermine $P_{crit}$ and $P_{opt}$, then the testing mode is executed in accordance with the testing protocol. As in a non-testing period, the operator has continuous access to the information from the feature extractor during a testing period to determine if it should continue to test for $P_{crit}$ and $P_{opt}$.

When the FIG. 1a auto-CPAP system enters the testing mode, a specific testing protocol of pressure perturbations is followed. Prior to identifying $P_{opt}$, the testing protocol is only interrupted if a large breathing variation, an apnea or hypoventilation is detected. The results from the non-testing mode and the testing mode are retained in the longterm memory.

b. Feature Extractor

The feature extractor (FE) is the center for continuous acquisition and analysis of data. For example, the feature extractor generates performance indices in response to respiratory airflow data. These performance indices are a measure of the pharyngeal airway's dynamic state and are used by the operator for decision making in both the testing and non-testing modes. In alternate embodiments, additional signals (e.g., monitoring signals related to oxygen saturation and sound) can be input to the feature extractor to assist in the continuous sensing of dynamic characteristics of the pharyngeal airway.

The feature extractor has two basic functional modules: a data acquisition module and a respiratory cycle analysis (RCA) module. In the exemplary FIG. 1a embodiment, data acquisition of the input signals (e.g., airflow) occurs via the 12 bit analog-to-digital converter 10 (e.g., Data Translation DT2821) every 8 msec.

The digital values are then passed into an RCA module where eight consecutive values are averaged to produce a single low pass filtered average value every 64 msec. Each 64 msec average value is then continuously analyzed in the RCA module for phase of respiration, apnea, and breath features. An important characteristic of the RCA module is that it continuously analyzes the airflow signal to identify the respiratory component (i.e., respiratory volume, RV) and the non-respiratory component (i.e., non-respiratory volume, n-RV).

Performance indices generated by the RCA module are updated continuously as follows, where the asterisks indicate a real time occurrence of an update for the feature listed:

| | During Inspiration | During Expiration |
|---|---|---|
| Respiratory phase | * | * (continually) |
| End of Breath | | * (end of expiration) |
| RCA Abnormalities | * | * (Excessive leak detection error and future error reporting) |

-continued

| | During Inspiration | During Expiration |
|---|---|---|
| Apnea | * | * |
| Breath Features: | | |
| $T_i$ | | * (time of inspiration) |
| $T_e$ | * | (time of expiration) |
| $T_{tot}$ | | * (total time of breath) |
| $Vol_i$ | | * (inspiratory volume) |
| $Vol_e$ | * | (expiratory volume) |
| $V_m$ | | * (mean inspiratory airflow) |
| $V_p$ | | * (peak inspiratory airflow) |
| Flatness | | * (measure of inspiratory flatness) |
| Roundness | | * (measure of inspiratory roundness) |

As mentioned previously, an optimum pressure is determined by evaluating the effects of incremental pressure perturbations on inspiratory airflow. Accordingly, the RCA module is designed to continuously report breath changes in upper airway state (i.e., to identify respiratory phase and end of breath conditions based on extracted features). A breath is defined as an inspiratory period followed by an expiration period. Therefore, an end of breath condition is updated at the end of expiration.

When the RCA module detects a problem, then an RCA abnormalities condition is set. For example, an abnormal condition is set either during inspiration or expiration when excessive flow leakage is detected. Further, the RCA module is designed to continuously report detection of apneas based on extracted features.

The breath features listed above are the dynamic physiological characteristics of the pharyngeal airway. Their variation, especially in combination, are excellent measures of the pharyngeal airway behavior. Values of $T_i$, $T_e$, $T_{tot}$, $Vol_i$, $Vol_e$, $V_m$ and $V_p$ (defined in the above table) are physiologically self explanatory breath features. Flatness and roundness values are breath features which are developed as measures of inspiratory airflow. The flatness and roundness values are used in accordance with preferred embodiments to identify pharyngeal airway behavior.

For purposes of the present discussion, flatness is defined as the relative deviation of the observed airflow from the mean airflow. In a preferred embodiment, individual values of airflow are obtained between 40% and 80% of the inspiratory period. The mean value is calculated and subtracted from the individual values of inspiratory flow. These individuals differences are squared and divided by the total number of observations minus one. The square root of this product is used to determine a relative variation.

The relative variation is divided by the $V_m$ to give a relative deviation or a coefficient of variation for that breath. This measure of airflow therefore represents a measure of flatness over the mid-range of inspiration. A relatively low value is used to indicate that inspiratory airflow during mid-inspiration is relatively constant. The common cause of this is flow-limitation secondary to pharyngeal collapse. Thus, a low value indicates the need for higher nasal CPAP pressures.

For purposes of the present discussion, the roundness feature supplies information regarding the similarity between the normalized inspiratory flow profile and a sine wave normalized for observed inspiratory time and for observed peak flow. The airflow predicted from the sine wave, Vsine, is calculated from the following normalized sine wave equation:

$$Vsine = Vpeak * sine(F*\pi)$$

where Vpeak is observed peak flow and F equals the fraction of inspiratory time elapsed. This equation for predicting sequential airflow measurements is used when the ratio of peak flow to $T_i$ is less than 1.1 and greater than 0.45. For values of the ratio greater than 1.1 the peak is estimated by multiplying $T_i$ by 1.1, and for values below 0.45 the peak is estimated by multiplying $T_i$ by 0.45.

The differences between consecutive values of observed inspiratory airflow and that calculated from the sine wave equation value are squared and summed, and then divided by the total number of points. The square root of this product is then divided by the mean value of airflow for that inspiration to give a normalized value for that breath.

Accordingly, the roundness index provides an estimate of the degree to which the inspiratory airflow profile resembles a sine wave. As flow limitation occurs or as the airflow signal becomes less sinusoidal, the roundness feature becomes larger. This indicates an increase in upper airway resistance and suggests that mask pressure may not be adequate.

Figure 2:
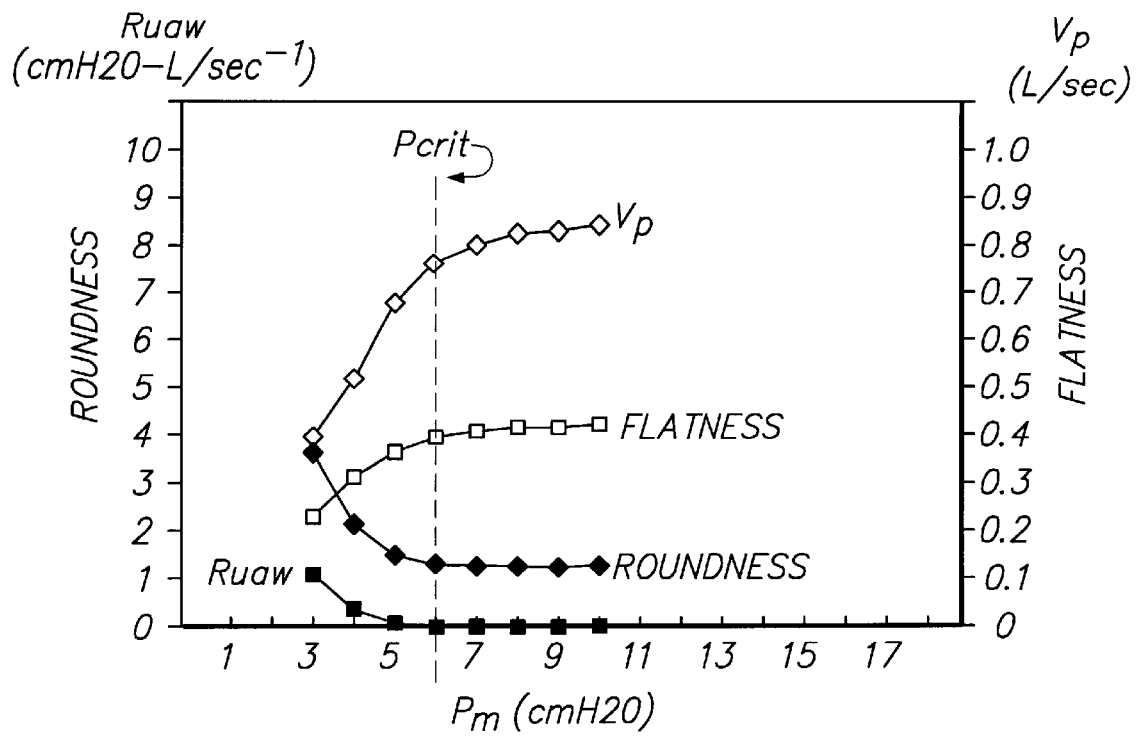
FIG. 2 shows a graph of characteristic features and upper airway resistance versus mask pressure for one particular mechanical condition of a simulated pharyngeal airway.
Figure 3:
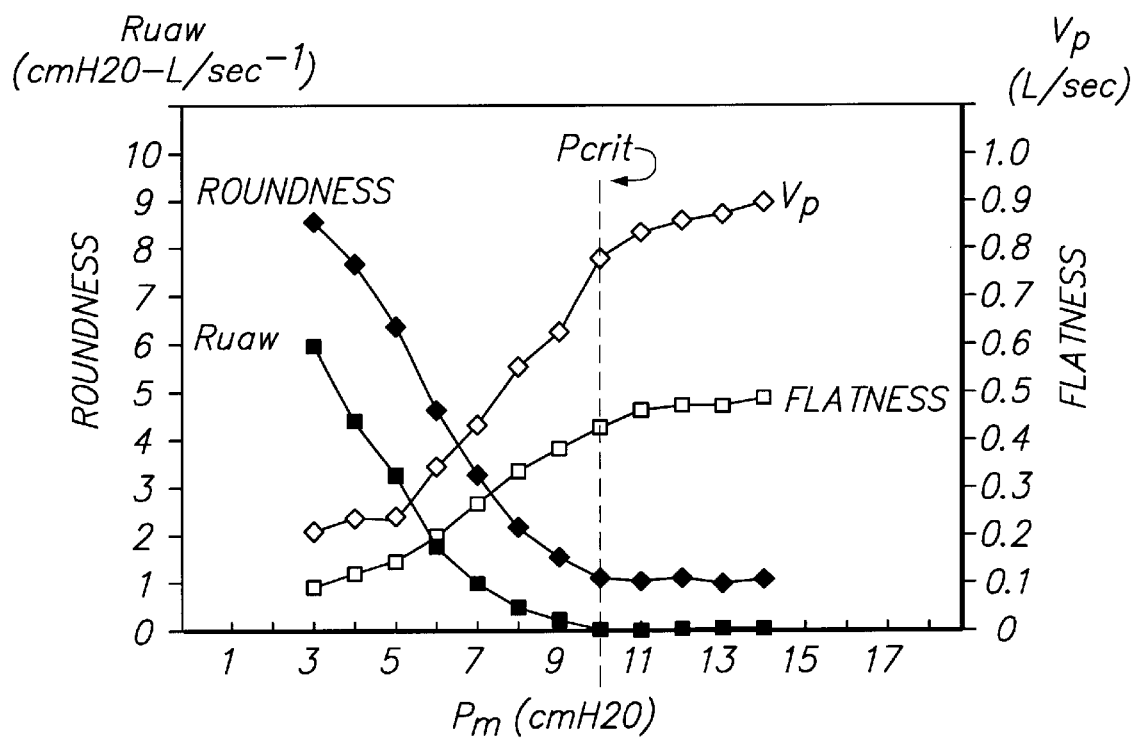
FIG. 3 shows a graph of characteristic features and upper airway resistance versus mask pressure for a second mechanical condition of the simulated pharyngeal airway.

FIGS. 2 and 3 illustrate a relationship between the characteristic features $V_p$, flatness, roundness, and upper airway resistance ($R_{uaw}$) versus mask pressure ($P_m$) The values presented are from a starling resistor model of the pharyngeal airway.

In FIG. 2, the pressure surrounding the collapsible tube ($P_s$) is 6 cmH$_2$O, whereas in FIG. 3, the $P_s$ is 10 cmH$_2$O. For values of $P_m$ greater than $P_s$, the features are represented by values which are at their minimum (e.g., roundness) or maximum (e.g., flatness and $V_p$), with $R_{uaw}$ being zero. For values of $P_m$ below $P_s$, as $R_{uaw}$ rises the features dramatically rise or fall. These results indicate that $V_p$ and flatness are measures of flow limitation and roundness is a measure of increasing upper airway resistance.

To update the performance indices and other information presented in the above chart, the RCA module includes the aforementioned respiratory phase threshold detection mechanism (TDM). The threshold detection mechanism detects the inspiratory and expiratory phase changes in airflow. The accuracy of the feature extraction is very dependent upon accurate detection of the start of inspiration. In accordance with preferred embodiments, the start of inspiration is ascertained solely from airflow.

Basic assumptions in the threshold detection mechanism are that inspiratory and expiratory volumes are approximately equal. Two factors affect the volumes causing them to be unequal. The volume of oxygen consumed per unit time is normally greater than the volume of carbon dioxide that is produced by the body. Further, breath-to-breath variation in tidal volume and timing during sleep, as well as arousal which alters alveolar ventilation and exact expiration volume, can result in a variation between inspiratory and expiratory volumes.

Normally the inspiratory tidal volume is 4% greater than the expiratory tidal volume. Over a 30 second period of quiet breathing, all variations can be approximately averaged out of this ratio. Therefore, a resultant average respiratory flow can be used as a basis to estimate the beginning of inspiration and to approximate non-respiratory flow.

When breathing without a bias flow, the actual start of inspiratory flow can be detected when the airflow signal crosses a no-flow value. This is because the actual zero respiratory flow corresponds to the zero flow value.

The characteristic increase in slope of flow which marks the onset of inspiration occurs even in the presence of non-respiratory flow. However, when a non-respiratory flow exists, pneumotach zero flow and zero respiratory flow are not the same as the non-respiratory flow constitutes a continuous flow through the pneumotach.

Accordingly, when a bias flow is present, the non-respiratory component of airflow must be determined to accurately identify the start of inspiration and the derived features. As mentioned above, the non-respiratory component is defined as that component of airflow not due to normal respiratory airflow. This non-respiratory airflow includes two components: the first is a known component due to the bias flow out the exhaust port of the nose mask used for washing out end tidal CO2 from the mask.

The second is a variable, unknown flow due to leaks around the mask or out of the patient mouth. The magnitude of this unknown flow is calculated and is used to establish times when the feature extractor may be in an unstable period such that information from the feature extractor may be inaccurate. More particularly, changes in the exhaust flow out of the mask due to pressure changes can be measured. A percent change in exhaust flow due to a pressure change can then be used to estimate a similar percentage change in total non-respiratory airflow during system operation.

The threshold detection mechanism for determining the onset of inspiration and expiration is highly dependent on the determination of the non-respiratory component. If the computed non-respiratory component is not within the specific range of the actual zero respiratory flow, then the resultant breath features are inaccurate. Corrections can be made during a non-testing mode or a testing mode up to a maximum of 1.6 L/sec and down to a minimum established by the known exhaust flow for the present mask pressure.

When the value for the average respiratory flow approximates the actual zero respiratory flow in the presence of mask exhaust flow and leak flow, the start of inspiration can thus be estimated using the change in slope as a characteristic marker. A lower limit can be attached to the determination of the start of inspiration by using a rule that inspiratory flow cannot occur below the known flow through the exhaust port. The following are exemplary preferred rules for estimating the start of inspiration and expiration.

Onset of Inspiration:
1) Average respiratory flow is used to approximate a range of flow where inspiration will mostly occur.
   a. Average respiratory flow is primarily derived by an ongoing digital averaging of respiratory flow for a 64 sec window of time.
   b. The mean value of four (4) successive estimations of the start of inspiration are determined. These four mean values are averaged into the average respiratory flow with a weight of 32 secs.
2) A range around the average respiratory flow of −0.05 L/sec and +0.1 L/sec is used to approximate the most likely occurrence of the start of inspiration.
3) While in expiration and within the above range, the start of inspiration is, in a preferred embodiment, Tentatively True when:
   a. The slope of the present 64 msec flow sample is greater than 0.39 L/sec and the slope of the previous 64 msec flow was below 0.30 L/sec,
   b. the slope of the present 64 msec flow sample is greater than 0.39 L/sec and the slope of the previous 64 msec flow was also greater than 0.30 L/sec, or
   c. the flow has exceeded the upper limit of the range, 0.1 L/sec above the average respiratory flow, and d. the estimated start of inspiration is above
   (1) the intentional leak for the present mask pressure during a $P_{crit}$ search, and
   (2) during a $P_{opt}$ search, the average respiratory flow.
4) The start of inspiration is True when:
   a. The slope remains above the upper limit of average respiratory flow (+0.1 L/sec), or
   b. A minimum slope of 0.27 L/sec is maintained for 0.42 secs.
5) The actual start of inspiration is estimated to occur at the previous flow rate when the start of inspiration was Tentatively True.

Onset of Expiration:
1) The same flow rate that was estimated for the start of inspiration is used as the start of expiration.

The continuous adaptation of averaged respiratory flow to changes in the non-respiratory flow (leaks) is made by several mechanisms. First, the averaged respiratory flow value is continuously calculated as a moving average using the 64 msec value of flow over a 64 sec window of time. This method produces a very constant value of average respiratory flow. Second, the use of an averaged start of inspiration as a weighted factor in the calculation of the averaged respiratory flow results in quicker adaptation of the threshold detection mechanism to moderate leaks that occur over an approximate 32 sec period. In addition, the averaged respiratory flow is re-initialized to the new mask pressure by: 1) prior to changing mask pressure, a ratio is found from the existing average respiratory flow divided by the present mask pressure, 2) the mask pressure is changed, then 3) the averaged respiratory flow is re-initialized to the new mask pressure times the ratio.

In the case of a sudden leak which could send the total airflow above the threshold detection mechanism, the result can erroneously be detected as an apneic event even though respiratory changes are occurring in the flow signal. In this case, when no change in respiratory phase has occurred for five (5) seconds then the highest and lowest airflow values are searched for the remaining 5 seconds of the 10 seconds limit for an apnea determination. Before an apnea condition is flagged true, if the difference between the highest and lowest airflow is greater than 0.3 L/sec, then an apneic condition is not flagged and the averaged respiratory flow is re-initialized to the midpoint between the highest and lowest airflow found in the last five (5) seconds of the apnea test. This last mechanism is designed to adapt to rapid changes in non-respiratory airflow due to leaks that may appear as an apnea to the feature extractor.

Around the average respiratory flow, the method of detecting inspiratory and expiratory flow minimizes the computational load in deciding phase changes and maximizes the accuracy of the pattern recognition.

C. Testing Protocol

During testing periods, the adaptive control system first reduces pressure and determines $P_{crit}$. This constitutes a characteristic lower limit of mask pressure for a given state of the patient's pharyngeal airway (e.g., sleep stage, position, and so forth). Having established this lower limit of pressure, the optimum higher pressure value $P_{opt}$ is determined by progressively increasing intra-pharyngeal pressure. The increases in peak inspiratory pressure and changes in shape of inspiratory airflow profile are recorded and used to identify $P_{opt}$.

The determination of $P_{crit}$ during a testing period is termed the $P_{crit}$ search. The subsequent determination of $P_{opt}$ during a testing period is termed the $P_{opt}$ search. Each search consists of a progressive series of incremental changes in mask pressure (i.e., step decreases for $P_{crit}$ and step increases for $P_{opt}$).

During a preferred search to identify $P_{crit}$ there are two types of pressure decreases that are performed when normal rules of operation have been satisfied. The first is a 4 cmH$_2$O decrease in mask pressure ($P_{crit}$ scan) which is used to test the pharyngeal airway for significant collapsibility before a $P_{crit}$ search actually begins. The scan begins at a holding pressure (Ph) used during the preceding non-testing period. If the information from the feature extractor during the $P_{crit}$ scan indicates that a significant airflow limitation has occurred, then a limit to subsequent $P_{crit}$ searching is set (4 cmH$_2$O below the holding pressure). This limit prevents excessive searching for the pressure which produces insignificant flow limitation.

The second type of pressure decrease that is performed when the rules of operation have been satisfied is referred to herein as the $P_{crit}$ search. A $P_{crit}$ search is performed after a $P_{crit}$ scan. During the $P_{crit}$ search, the pressure perturbations are a series of 2 cmH$_2$O decreases in mask pressure.

A test for $P_{crit}$ during a $P_{crit}$ search is repeated until predetermined decision criteria have been met (i.e., changes in peak inspiratory airflow and/or profile shape features detected by the feature extractor exceed predetermined decision criteria) or until a limit to the $P_{crit}$ search set by the $P_{crit}$ scan is encountered. Each $P_{crit}$ test is initiated with a pre-test period which is followed by a single breath test period and a five breath post-test period. However, when the decision criteria for the $P_{crit}$ search have been satisfied during the single breath test, there is no post-test period.

The $P_{opt}$ search is a series of tests or increases in mask pressure (e.g., 2 cmH$_2$O) which is initiated after $P_{crit}$ has been determined. The search for $P_{opt}$ involves finding the mask pressure at which the peak flow and the flow profile do not improve after a 2 cmH$_2$O increase in mask pressure. Thus, the minimum effective CPAP pressure represents that mask pressure at which there is no improvement in the flow profile after a worsening in the flow profile.

Each $P_{opt}$ test is initiated with pre-test similar to that of a $P_{opt}$ pre-test. A single breath test period and a five breath post-test period follow the pre-test. In a $P_{opt}$ search, the post-test is used to detect an unadjusted non-respiratory flow error.

An unadjusted non-respiratory flow error is detected in the $P_{opt}$ search when the non-respiratory flow of a 5th breath detected during the post-test is greater than that of a 1st breath detected during the post-test (e.g., by 0.03 L/sec as described above with respect to the feature extractor) following an increase in mask pressure. If an unadjusted non-respiratory flow error was not detected, then the five breaths of the post-test period are use as pre-test values and a single breath test is performed immediately after what was the post-test period. If an unadjusted non-respiratory flow is detected then a pre-test period is performed unless at least one $P_{opt}$ test has been performed. If one $P_{opt}$ test has been performed and there is an unadjusted non-respiratory leak then $P_{opt}$ is deemed to have been found and testing is stopped. The pre-test period after a post-test in the $P_{opt}$ search allows for non-respiratory adjustments.

A $P_{opt}$ search continues provided normal rules of operation are met until predetermined decision criteria for a minimum effective CPAP have been met. If an unadjusted non-respiratory error has occurred and at least one $P_{opt}$ test has been performed, then $P_{opt}$ is determined to have been found at the present pressure and the current testing mode is exited.

In any test, if the decision criteria for a flow alone condition was exceeded ($P_{crit}$) or not exceeded ($P_{opt}$), then the test is repeated. A flow alone condition corresponds to a relatively large change in peak airflow with little or no relative change in roundness and/or flatness. If an apnea, hypoventilation or respiratory variation error is detected during the testing, the testing mode is exited and the system goes directly to the holding pressure of the previous non-testing period.

The decision criteria for $P_{crit}$ are considered to have been satisfied if a relative change in extracted features exceeds the predetermined decision criteria (DC) in any one of four ways: (1) difference between feature values extracted during a first breath test and currently established pre-test feature values exceed the DC; (2) difference between feature values extracted using an average of 4th and 5th breaths detected during the post-test (post-test average) and currently established pre-test feature values exceed the DC; (3) difference between feature values extracted during subsequent single test breaths and the initial pre-test feature values previously established during the initial pre-test exceed the DC; or (4) difference between feature values extracted during subsequent post-tests and feature values of the initial pre-test exceed the DC. The detection of $P_{crit}$ using the comparisons of (3) and (4) above is referred to herein as a trend test. While comparisons similar to (1) and (2) above are used to identify $P_{opt}$, the trend test comparisons are used only to determine $P_{crit}$.

More particularly, the trend test is used exclusively in the $P_{crit}$ search to detect a progressive decrease in the flow profile over the $P_{crit}$ search that may not show up during any one single breath test or post-test. As described above, the trend test uses the initial pre-test features (e.g., five breath average) as the template for subsequent comparisons during tests (3) and (4).

In an exemplary embodiment, a test is true during a $P_{crit}$ search if relative changes in the $V_p$ feature and the flatness feature or relative changes in the $V_p$ feature and the roundness feature have exceeded the DC. Similarly, during a $P_{opt}$ search, if relative changes in the $V_p$ feature and the flatness feature or relative changes in the $V_p$ feature and the roundness feature changes have not exceeded the DC, the test is true.

As described above, the process of decision making during the search for $P_{crit}$ and $P_{opt}$ is based on a comparison of relative changes in extracted features with the actual DC for each feature. The DC are determined by modifying significant decision criteria (SDC) with significant decision modifiers (SCDM) that depend upon the mask pressure.

Prior to starting the auto-CPAP system, SDC are established for each feature for both the $P_{crit}$ and $P_{opt}$ search. Exemplary SDC values are:

|  | $P_{crit}$ | $P_{opt}$ |
|---|---|---|
| $V_p$: (flow only) | 0.24 | 0.20 |
| $V_p$: (combine with below) | 0.21 | 0.20 |
| Flatness: | 0.24 | 0.20 |
| Roundness: | 0.40 | 0.20 |

The SDC are preselected values for the relative change in peak inspiratory flow and/or profile shape indices. The SDC are the basic standards used for comparison with observed changes in peak inspiratory flow and/or profile shape indices during the $P_{crit}$ and $P_{opt}$ searches. The SDCM is a factor which varies as a function of mask pressure (FIG. 4) and modifies the DC values so that the actual or operational decision criteria varies in accordance with statistical probability.

Figure 4:
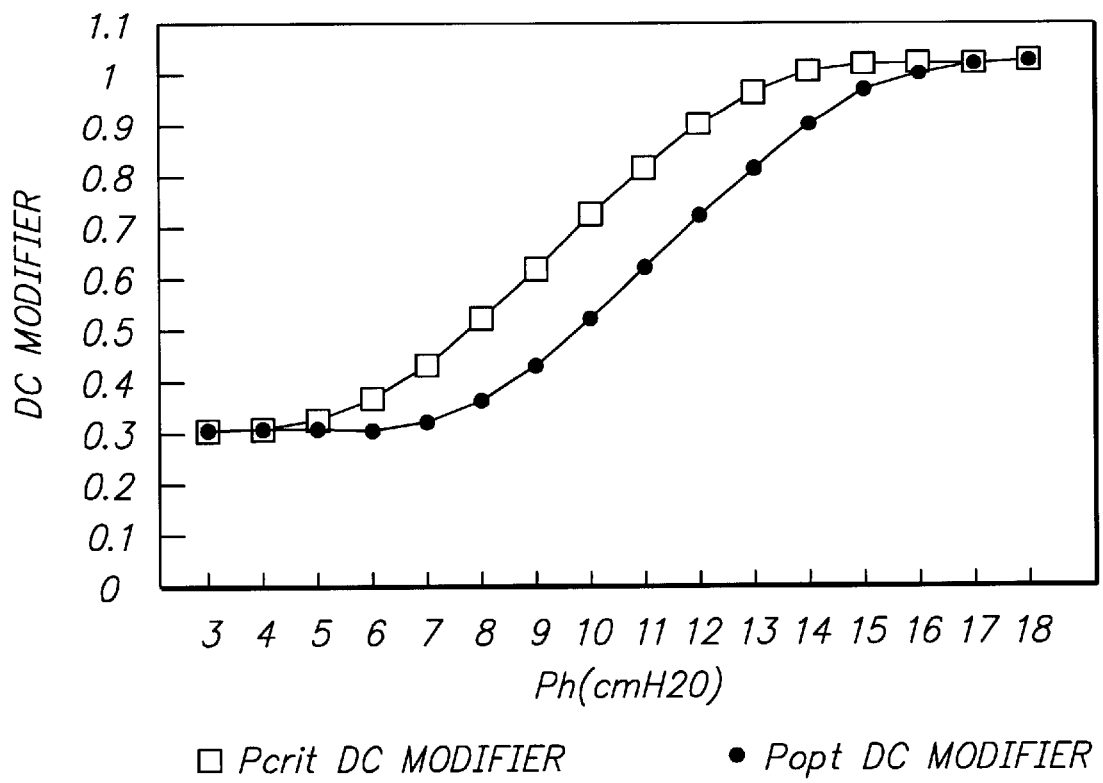
FIG. 4 shows a graphical representation of decision criteria modifiers used in conjunction with an exemplary embodiment of an adaptive controller.

The above SDC's for each feature and search are modified depending upon the mask pressure at the time of the test by multiplying the SDC with the decision criteria modifiers (SDCM). FIG. 4 illustrates exemplary modifiers used on the SDC. In FIG. 4, the abscissa corresponds to mask pressure values while the ordinate corresponds to SDCM values.

Two SDCM curves are presented in FIG. 4. One is for the $P_{crit}$ search and the other is for the $P_{opt}$ search. During the $P_{crit}$ search, as the mask pressure is reduced, the modifier becomes less and the criteria to be exceeded becomes less. Therefore, it becomes easier to find $P_{crit}$ with less test pressure. Conversely, during the $P_{opt}$ search, the SDCM becomes higher and it becomes easier to find a change less than the modified SDC.

The DC for $P_{crit}$ and $P_{opt}$ are derived by a formula that incorporates the SDC and the SDCM. The SDC for each performance index and desired combinations of SDC's are set for $P_{crit}$ and $P_{opt}$. The DC formula for each performance index is calculated as follows:

$$DC = SDC \times SDCM$$

As an adaptive control system, the auto-CPAP has several mechanisms to maintain and improve optimal performance and reliability. One such exemplary mechanism is the modifying the SDCM to establish an optimum range where the likelihood or probability of finding $P_{crit}$ and $P_{opt}$ for each patient is highest. Another mechanism is the continuous adjusting of the estimation of the non-respiratory flow as described previously.

This latter mechanism has several features that act to optimize the detection of inspiration. The first is a weighting of estimations of the start of inspiration into a moving average of airflow. The second is the immediate re-initializing of the moving average of airflow when the mask pressure is changed and a leak condition has occurred but a change in respiration is not detected. Another exemplary optimizing feature is weighting the performance indices and their combinations to increase accuracy of establishing $P_{crit}$ and $P_{opt}$.

The single best manner of maintaining reliability is to operate within the normal rules of operation. The rules can be modified if a particular problem is repeatedly encountered (e.g., leaks) to ensure performance indices are correct. The SDC, SDCM, and the normal operating rules can also be modified by additional external inputs. For example, the FIG. 1a system can operate with known monitors that are used in the diagnosis of OSA. One such commercially available oxygen saturation and snoring monitoring device is a portable sleep apnea monitor known as MESAM, available from Healthdyne Technologies of Marietta, Ga., USA. Inputs from this, or other monitors, can be input to the FIG. 1a adaptive control system along with the airflow signal.

As will be described in greater detail during a discussion of system operation below, a search for $P_{crit}$ begins with the scan protocol. As mentioned above, an exemplary scan is a single 4 cmH$_2$O decrease in mask pressure. This single breath decrease is preceded by 5 breaths. The mask pressure during the 5 breaths which precede the pressure drop of a scan is either the holding pressure during the non-testing period, or the last test pressure during a $P_{crit}$ search if the scan protocol is repeated during a $P_{crit}$ search.

The average values from the features during the pre-pressure drop of a scan are used as control values during the scan. If the comparison between the 5 breath average and the post pressure drop during a scan is significant (as determined by the DC), the system records that the scan was significant and the post scan pressure becomes the limiting pressure during the $P_{crit}$ search (4 cmH$_2$O below present holding pressure).

The search protocol begins with the search for $P_{crit}$ at the same holding pressure as the preceding scan (i.e., prior to the 4 cmH$_2$O drop). The search protocol begins with a pre-test during which 5 breaths prior a pressure decrease are averaged and used as controls for comparisons during subsequent single breath tests and post-tests. Following the pre-test breaths, the pressure is dropped 2 cmH$_2$O and the subsequent inspiratory breath features are collected.

If the breath features during the decrease in pressure did not exceed the DC set for this level of mask pressure, then the mask pressure is left unchanged and a post-test period begins consisting of 5 breaths. The fourth and fifth breaths of this post-test period are averaged (i.e., post-test average) and the average is tested to see if it exceeded the same DC of the single breath test. If the DC is exceeded in either the single breath test or the post-test average, then the mask pressure is returned to the mask pressure set during the pre-test period and a $P_{opt}$ search is initiated.

If neither the single breath test nor the post-test average exceeded the DC, then another test is performed, in this case a $P_{crit}$ test. Accordingly, during a subsequent single breath test and post-test, a trend test will be used to compare extracted features with features of the initial pre-test average. These comparisons are performed in addition to comparisons of extracted features with the current pre-test average as discussed above.

In an exemplary embodiment, if a second cycle of a $P_{crit}$ search pre-test, single breath test, and post-test does not exceed the DC, or if the previous $P_{crit}$ scan was significant but the limiting pressure was not reached, then the scan protocol is repeated at the previous search mask pressure. This basic scan-search combined protocol is repeated until the lowest mask pressure is reached or until the comparisons exceed the test criteria. For example, if the initial scan was not significant and $P_{crit}$ has not been detected after two incremental pressure decreases, another scan will be performed. In this scan, an additional 4 cmH$_2$O pressure drop is introduced (i.e., total 8 cmH$_2$O drop). The aforementioned $P_{crit}$ search is then repeated.

An exemplary search protocol for $P_{opt}$ is slightly different than the search used to identify $P_{crit}$. A scan is not used in the testing protocol to identify $P_{opt}$. Further, during a preferred $P_{opt}$ search, a pre-test series of 5 breaths precedes an incremental increase in mask pressure. Further, the trend tests used to identify $P_{crit}$ are not used to identify $P_{opt}$. The $P_{opt}$ search protocol consists of 5 pre-test breaths, a 2 cmH$_2$O step increases in pressure, and an optional 5 post-test breaths if an unadjusted non-respiratory error was detected and if it was the first $P_{opt}$ test. This $P_{opt}$ protocol is repeated until no significant differences exist between $V_p$ and/or profile shape indices of the pre-test relative to the single breath test and the post-test, or until there is a unadjusted non-respiratory error and at least one $P_{opt}$ test.

Figure 5:
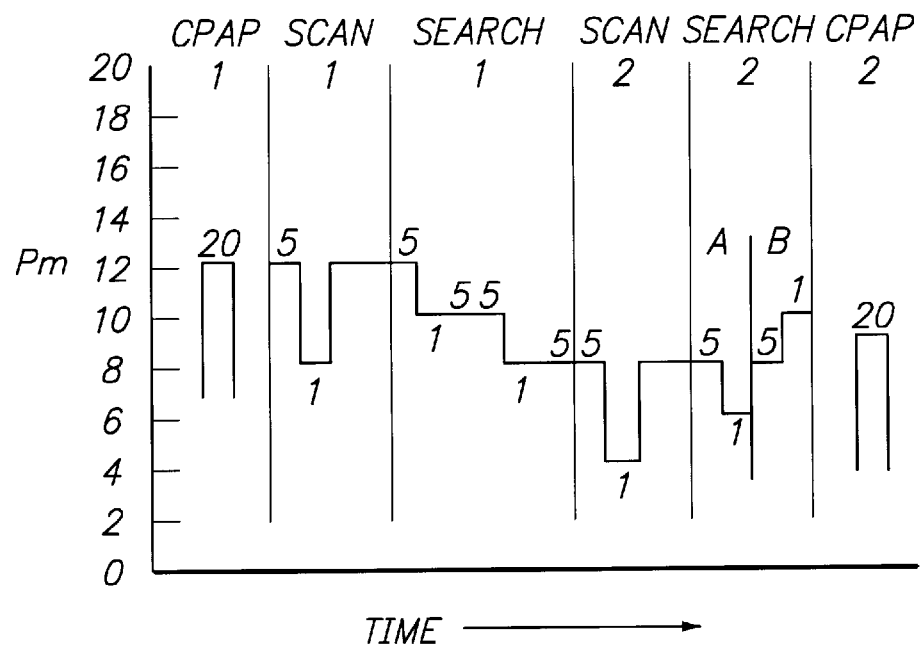
FIG. 5 shows an exemplary implementation of testing and non-testing modes of operation.
Figure 6A:
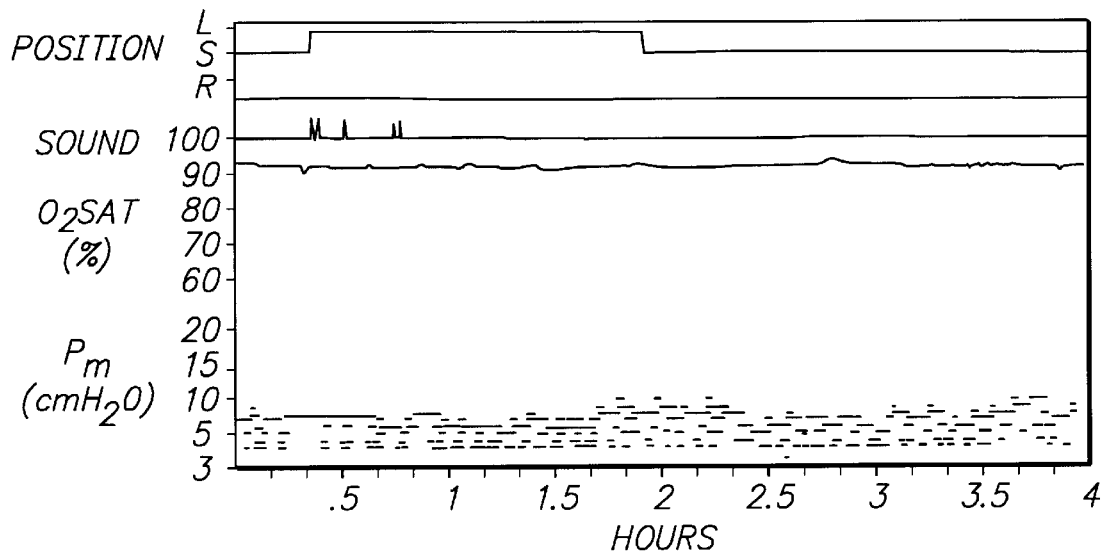
FIG. 6 shows a display of pressure (PM), microphone signal (sound), $O_2$ saturation ($O_2$ Sat) and body position (L: left side; R: right side; S: supine) in an OSA patient being treated with auto-CPAP.
Figure 6B:
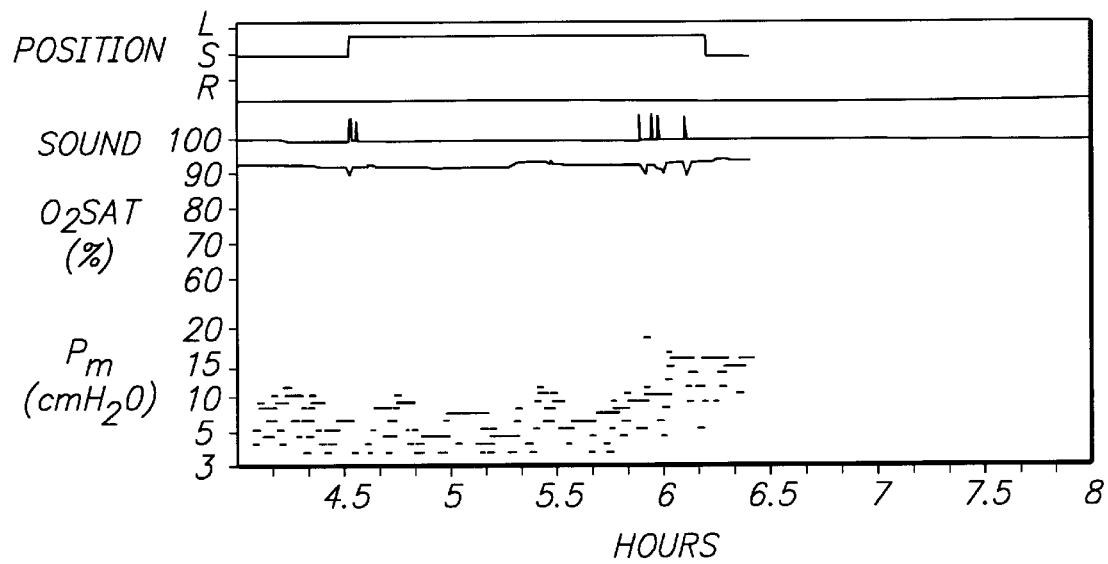

FIG. 5 illustrates exemplary scan and search pressure perturbation protocols in the search for $P_{opt}$. FIG. 6 shows an exemplary display of pressure, sound, oxygen saturation and body position in a patient being treated with auto-CPAP in accordance with a preferred embodiment. In FIG. 5, the x-axis is a compressed time scale while the y-axis is mask Pressure ($P_m$) from 0 to 20 cmH$_2$O. CPAP 1 period is a non-testing period where the Ph was 12 cmH$_2$O.

In the first scan protocol, scan 1 is shown with a 5 (5 breaths) above the line indicating the pressure of the pre-single breath test (1 below the pressure line). The pressure drop for the scan 1 was from 12 to 8 cmH$_2$O and held for one complete inspiratory period and then returned to the previous holding pressure. Scan 1 was not found to be significant. Therefore, the $P_{crit}$ scan limitation is not set, and $P_{crit}$ search 1 is initiated.

The first $P_{crit}$ search protocol begins with 5 breaths at the same holding pressure previous to the scan. As shown in FIG. 5, the $P_{crit}$ search was not significant for the next two successive decreases in mask pressure, and so a second scan protocol, scan 2, was initiated at the mask pressure of 8 cmH$_2$O. The second scan of the second scan protocol was significant (i.e., going from 8 to 4 cmH$_2$O). Thus, the scan was judged significant and the limiting pressure was set as 4 cmH$_2$O. During a subsequent $P_{crit}$ search, the first decrease in pressure, search 2A, did exceed the DC for the mask pressure of 6 cmH$_2$O. The search for $P_{crit}$ was therefore ceased and $P_{crit}$ was set to 6 cmH$_2$O.

The mask pressure was then returned to 8 cmH$_2$O and the search for $P_{opt}$ was started, search 2B. The first test for $P_{opt}$ resulted in no significant changes in the inspiratory features (i.e., no change in incrementing 2 cmH$_2$O, from 8 to 10 cmH$_2$O). Thus, the $P_{opt}$ search was stopped and the new holding pressure was set at 1 cmH$_2$O less than the last single breath test and post-test pressure (i.e., 9 cmH$_2$O).

d. Long Term Memory

The long term memory stores specific information for use by the physician or the Sleep Laboratory for diagnostic or for follow-up therapeutic applications. In addition to recording upper airway system characteristic features during system operation, stored information can be assembled to identify the patient's use of the auto-CPAP system (home use) or in diagnostic or therapeutic studies. This information can be used by the physician to assess the integrity of results obtained during home or lab use of the system.

3. System Operation

Figure 7:
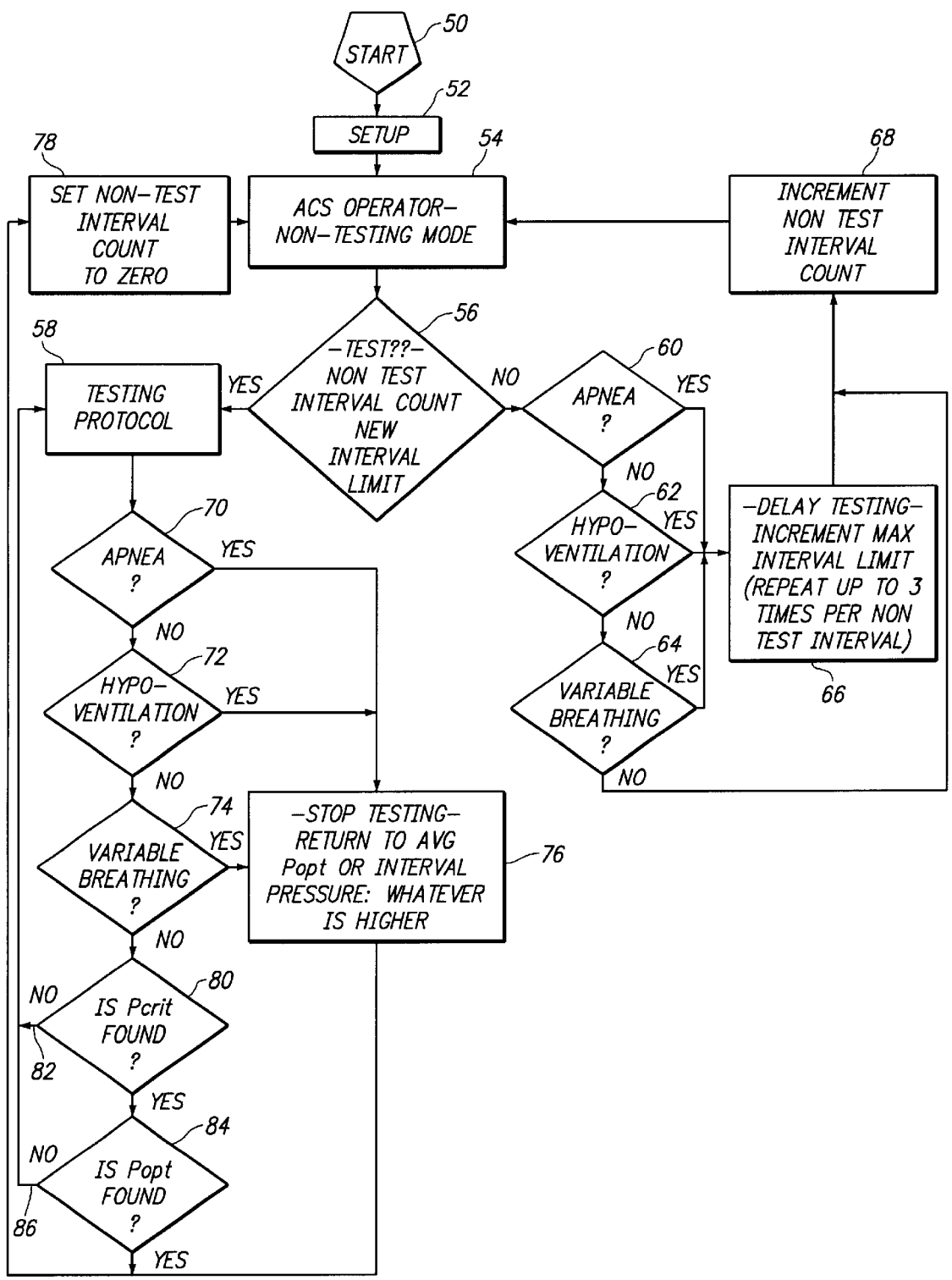
FIG. 7 shows a general flow chart of overall operation of a preferred embodiment.

A more detailed discussion of overall system operation and in particular, implementation of a preferred testing protocol, will now be provided. FIG. 7 shows a general flow diagram of an exemplary system operation. In block 50, the system is powered for use. In block 52, the system is initialized. This step includes setting all ports as desired on the adaptive control system 12.

Following start-up and initialization, the adaptive control system operator enters a non-testing mode as indicated by block 54. While in the non-testing mode, the operator continuously evaluates whether a testing mode can be entered to update $P_{crit}$ and $P_{opt}$. In a preferred embodiment, a test mode can be entered only after a predetermined number of breaths have occurred without the detection of breathing instabilities (e.g., apnea, hypoventilation or variable breathing).

An interval count is used to keep track of the number of breaths. Each interval count represents ten breaths. The interval count is compared to the maximum interval limit (block 56) which can range, in a preferred embodiment, from a minimum of two counts to a maximum of five counts. After five counts (i.e., 50 breaths), a decision is automatically made to enter a testing mode even though breathing instabilities may exist (block 56).

After two intervals (i.e., 20 breaths), if all rules are satisfied (i.e., no breathing instabilities) the testing protocol of block 58 is initiated. However, if all rules are not satisfied (i.e., apnea, hypoventilation and/or variable breathing is detected by decision blocks 60, 62 and 64), testing is delayed by increasing the maximal interval limit up to three times (block 66) and the non-test interval count is incremented (block 68). The system then remains in the non-testing mode for 10 more breaths.

Where breathing instabilities have been determined even after 50 consecutive breaths, the consistency of the instability is deemed sufficient to warrant initiation of a test mode. Thus, at any non-test interval count equal to or greater than maximum interval limit, a testing mode can be initiated (block 58).

During a testing mode, a search is first made for $P_{crit}$. Once $P_{crit}$ has been determined, a search is made for $P_{opt}$. In the testing mode, the system continuously checks for apnea, hypoventilation and/or variable breathing (blocks 70, 72 and 74). If any of these instabilities are detected (or any changes in these values are detected in the case where the test mode was entered after 50 breaths), testing is stopped (block 76). The non-test interval count is reset to zero (block 78) and the system returns to a non-test mode.

At this point, because neither $P_{crit}$ and $P_{opt}$ have been determined, the system uses the last, accurately determined $P_{opt}$ during the non-test mode (block 76). Alternately, the system can be set up such that block 76 represents use of a $P_{opt}$ determined as an average of prior (e.g., two) accurately determined $P_{opt}$. In yet another embodiment, an experimentally determined $P_{opt}$ previously specified by a sleep lab specialist can be used.

Assuming the test mode is not interrupted, a search for $P_{crit}$ is then performed (block 80). During, this search, the system continuously monitors breathing (loop 82) to detect instabilities which may influence accurate determination of $P_{crit}$. Once $P_{crit}$ has been determined, a search is made for $P_{opt}$ (block 84). Again, during the search for $P_{opt}$, continuous monitoring of breathing is performed (loop 86). When both $P_{crit}$ and $P_{opt}$ have been found, the system resets the non-test interval count to zero (block 78) and returns to a non-test mode (block 54).

Figure 8A:
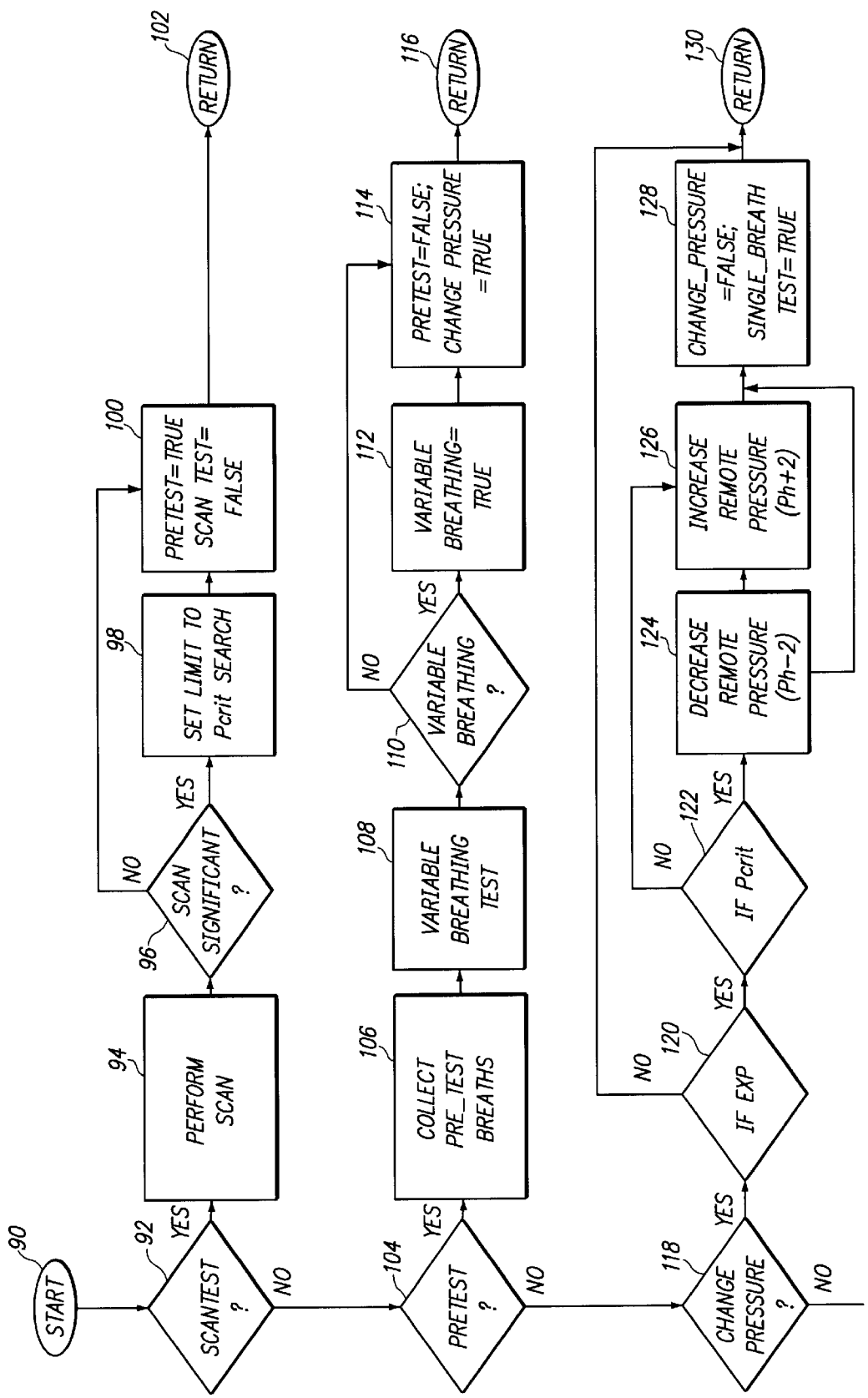
FIGS. 8a–c show a portion of the FIG. 7 flow chart in greater detail.
Figure 8B:
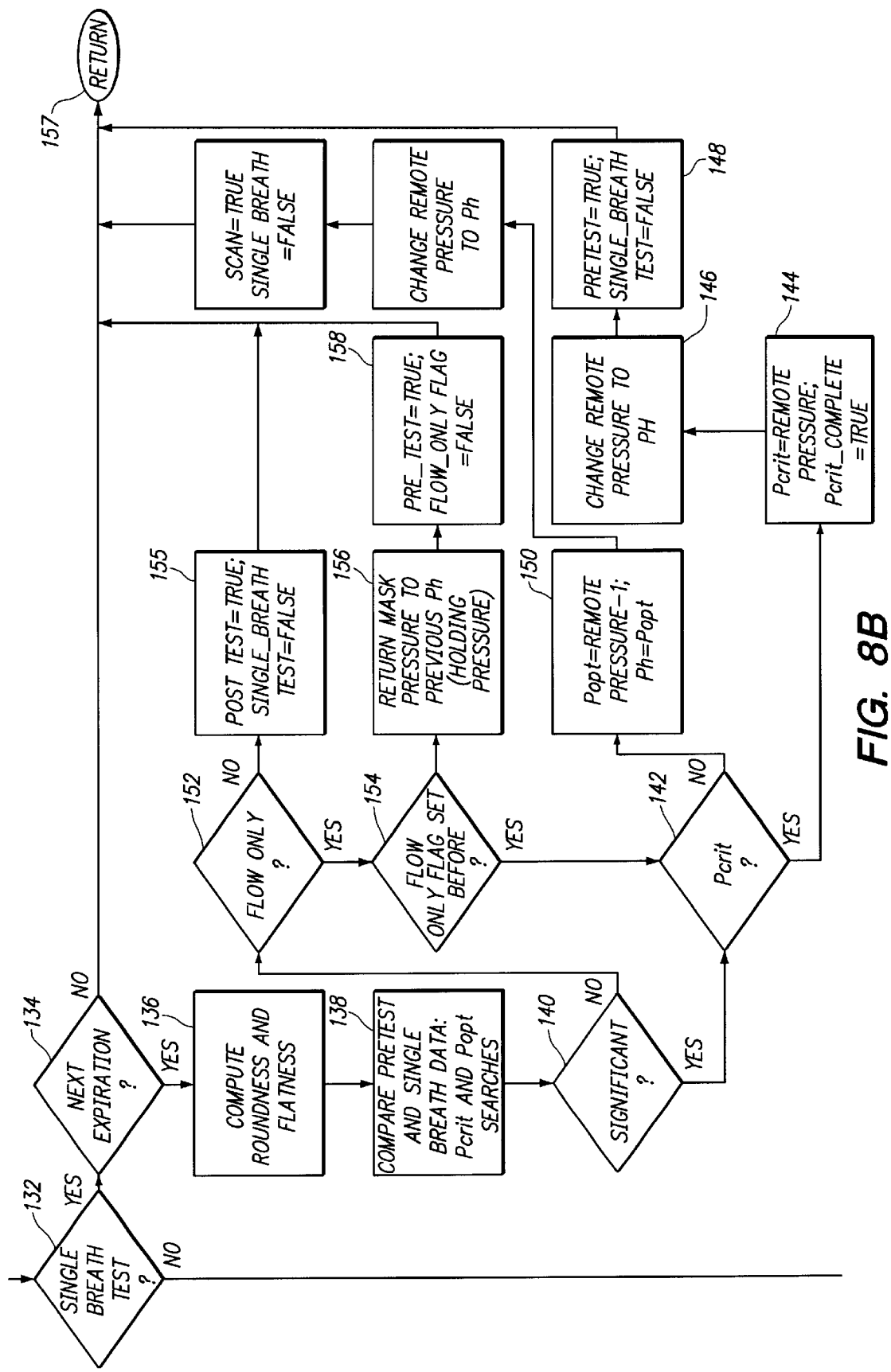
Figure 8C:
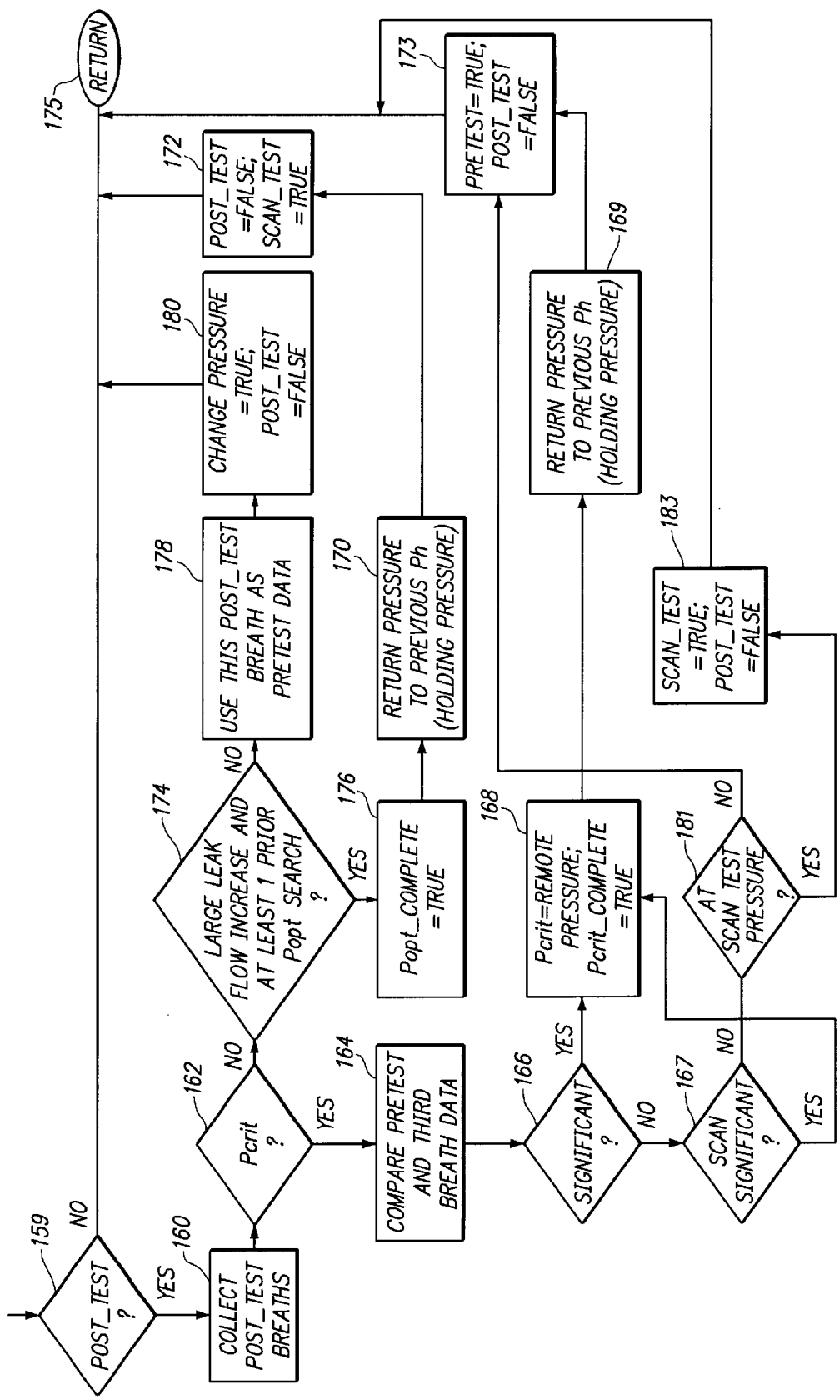

FIGS. 8a–c show a more specific flow chart of an exemplary testing protocol represented by block 58 in FIG. 7. The steps of the FIG. 8 flow chart are first executed to determine $P_{crit}$. Afterwards, the FIG. 8 steps are repeated to identify $P_{opt}$.

In FIG. 8a, once a test mode has been initiated (i.e., start block 90), a decision is made whether a scan test flag has been set TRUE to trigger a $P_{crit}$ scan (block 92). Assuming that the testing mode has just been initiated such that the scan test flag has not yet been set FALSE, a scan test is performed to initiate a $P_{crit}$ scan (block 94).

The scan test is used to determine whether a pressure drop of, for example 4 $cmH_2O$, from the pressure generating means results in a significant flow limitation. Throughout the scan test (and throughout all stages of the testing mode), a continuous monitoring of breathing is performed to detect instabilities (i.e., blocks 70, 72 and 74 of FIG. 7).

In block 96, assuming no breathing instabilities were detected, a decision of whether the scan was significant is performed. For this purpose, five breaths are collected and their features averaged. The averages are compared to features detected after the 4 $cmH_2O$ drop).

If the scan was significant, a scan significant flag is set TRUE (indicating that a lower limit for $P_{crit}$ has been established) and the pressure used prior to the 4 $cmH_2O$ drop is used to initiate a $P_{crit}$ search. To determine whether a scan was significant, a value of 1.1×DC is used (rather than the aforementioned FIG. 4 SDC and SDCM) since a relatively large pressure drop is used for the $P_{crit}$ scan.

In block 98, a pressure drop limit of, for example, 2 $cmH_2O$ is established to search for $P_{crit}$. In block 100, a pre-test TRUE flag is set to initiate a pre-test (block 104) and a scan test FALSE flag is set to indicate completion of a scan test.

Where the scan was not determined to be significant at block 96, the pre-test flag is nevertheless set TRUE and the scan test is set FALSE. Because the scan significant flag is not set TRUE, another scan can be subsequently initiated if $P_{crit}$ is not identified in response to two incremental pressure decreases.

Upon completion of the scan, a return (block 102) is made to start block 90. Since the scan test flag has been set FALSE, the system sequences to pre-test (block 104).

During a pre-test, information associated with five breaths is collected (block 106) for comparison with single breath information collected during a subsequent single breath test. Upon collecting the five breath information, the averages of the breaths are calculated and if this was the first or initial pre-test period the averages are saved for later comparisons in the trend tests. Following block 106, a variable breathing test is performed (block 108) during which collected information regarding five breaths is examined for variations. If the variations are significant (decision block 110), a variable breathing flag is set TRUE (block 112). Further, a pre-test completion flag is set FALSE and a change pressure flag is set TRUE (block 114).

The setting of the flags in block 114 causes the system to perform a change pressure sequence (block 118) following a return from the pre-test (block 116) to the start block 90. Where no variable breathing was detected at block 110, the variable breathing flag is not set TRUE prior to initiation of a change pressure sequence.

Once the scan test and pre-test flags have been set FALSE, the system sequences from block 90 to a change pressure sequence (block 118). In a change pressure sequence, the system awaits a start of expiration subsequent to the five breaths of the pre-test (block 120). The pre-test is similarly performed during a subsequent $P_{opt}$ search which is initiated after $P_{crit}$ has been determined.

At the onset of expiration during a $P_{crit}$ search (as determined at block 122), the remote holding pressure ($P_h$) from the pressure generating means is reduced, for example, 2 $cmH_2O$ (block 124). During a $P_{opt}$ search, the remote holding pressure is increased by, for example, 2 $cmH_2O$ (block 126). After a pressure change has been effected, a change pressure flag is set FALSE, and a single breath test flag is set TRUE (block 128) to initiate a single breath test (block 132) following a return block 130.

During a single breath test, the onset of a next sequential expiration is detected (block 134). Once this subsequent expiration has been detected, the feature extractor computes roundness and flatness (block 136) for the pressure set during the last pressure change. The pre-test and single breath data is then compared during the $P_{crit}$ test (block 138). A similar sequence is performed during a subsequent $P_{opt}$ test.

In block 140, a determination is made whether the results of the comparison in block 138 are significant. If significant and where $P_{crit}$ is being determined, $P_{crit}$ is set to the current holding pressure and a $P_{crit}$ search complete flag is set (blocks 142, 144). The remote pressure is then set to the holding pressure prior to the change in pressure (block 146), a pre-test flag is set TRUE to initiate a $P_{opt}$ pre-test and a single breath test flag is set FALSE (block 148).

During a $P_{opt}$ search, $P_{opt}$ is set to the remote pressure minus, for example, 1 $cmH_2O$ (block 150). Further, a $P_{opt}$ search complete flag is set TRUE, and the holding pressure is set to the new value of $P_{opt}$ (block 150).

Where the results of the comparison in block 140 were not significant, a determination is made as to whether a flow alone condition exists (block 152) or whether a flow only flag has been set TRUE (block 154). A flow alone condition is considered to exist when there is a significant change in peak airflow but features of roundness and flatness have not changed significantly. When a flow alone condition exists for two consecutive testing cycles during either a $P_{crit}$ test or a $P_{opt}$ test, $P_{crit}$ or $P_{opt}$ are set in blocks 144 and 150, respectively. A flow only flag is set TRUE after a first flow alone condition so that a second consecutive flow alone condition can be detected (block 154). Where a second flow alone condition has not yet occurred, pressure is returned to the previous holding pressure, the pre-test flag is set TRUE and the flow only flag is set TRUE (blocks 156 and 158).

Where the comparison in blocks 138 and 140 was not significant, and a flow alone condition had not been established (block 152), a post-test flag is set TRUE to initiate a post-test (block 155) following a return (block 157). Further, a single breath complete flag is set FALSE (block 155) so that the system will transition to the post-test at block 159.

Assuming the scan, pre-test, change pressure and single breath flags are all set FALSE, a post-test is initiated (block 159). During a post-test, a predetermined number of post-test breaths are collected (block 160). For example, five breaths are collected for a $P_{crit}$ search, the last two of which are averaged (blocks 162, 164). A determination is then made of whether this average is significant (block 166).

If the average is significant (i.e., significant flow limitation of the pharyngeal airway), $P_{crit}$ is set to the remote pressure and a $P_{crit}$ search complete flag is set TRUE (block 168). The pressure from the pressure generating means is then reset to the previous holding pressure (block 169) so that the significant flow limitation is not maintained. Further, a $P_{opt}$ search is initiated by setting the pre-test flag TRUE (block 173). The pre-test and post-test flags are also set FALSE (block 173) to permit subsequent re-initiation of a post-test during a $P_{opt}$ search.

If the outcome of block 166 was a negative during the $P_{crit}$ search, then a determination is made as to whether the $P_{crit}$ scan was significant. If so then control flows to block 168 since the next 2 cmH$_2$O pressure decrease would set $P_{crit}$ to the significant pressure limit of the scan test in the exemplary embodiment described herein (i.e., this example uses a 4 cmH$_2$O scan decrease and 2 cmH$_2$O $P_{crit}$ search decreases). In this case, $P_{crit}$ is set to the scan test pressure.

If the outcome of the block 167 was negative then in block 181 a determination is made as to whether the pressure has been decreased to the scan test pressure (i.e., previous holding pressure minus 4 cmH$_2$O). If the pressure has not yet been decreased to the scan test pressure, control flows to block 173 to initiate another $P_{crit}$ search without executing a scan. However, if the pressure is at the scan test pressure, the scan test flag is set to TRUE (block 183), and the program flow prepares for another $P_{crit}$ scan (e.g., with a holding pressure that will now be 8 cmH$_2$O below the original holding pressure of the initial scan).

Where the post-test breaths at block 160 were acquired during a $P_{opt}$ search, a determination is made as to whether a prior increase in pressure during a $P_{opt}$ search resulted in a large increase in flow leakage out of the mask after at least one prior $P_{opt}$ test has been completed (block 174). If so, then the $P_{opt}$ search complete flag is set TRUE (block 176) and pressure is returned to the previous holding pressure at which a large increase in leakage was not detected (block 170). Further, the scan test flag is set TRUE for the next series of $P_{crit}$ and $P_{opt}$ searches, the pre-test flag is set FALSE and the post-test flag is set FALSE (block 172).

If a large flow leak was not detected during a $P_{opt}$ post-test (block 174), the post-test breaths are used as pre-test data (block 178), and a change pressure request flag is set TRUE (block 180). This causes another incremental increase in pressure and another $P_{opt}$ test in an effort to identify $P_{opt}$.

Following a detection of $P_{crit}$ and $P_{opt}$ during a testing protocol, the system returns to a non-testing mode as indicated by block 78 in FIG. 7. A testing mode is then re-initiated in accordance with decision block 56 to adaptively update $P_{crit}$ and $P_{opt}$.

It will be appreciated by those of ordinary skill in the art that the present invention can be embodied in other specific forms without departing from the spirit or essential character thereof. The presently disclosed embodiments are therefore considered in all respects to be illustrative and not restrictive. The scope of the invention as indicated by the appended claims rather than the foregoing description, and all changes which come within the meaning and range of equivalents thereof are intended to be embraced therein.

What is claimed is:

1. Method for adaptively providing continuous positive airway pressure in an upper airway system comprising the steps of:
   detecting airflow in the upper airway system in predetermined increments of time;
   averaging said airflow information over a second period of time;
   distinguishing respiratory and non-respiratory components of said airflow using said averaged information;
   identifying periods of inspiration and expiration using said non-respiratory flow information;
   extracting features of said upper airway system during at least one of said periods of inspiration;
   identifying airflow profiles based on said detected airflow and said extracted features;
   determining a critical pressure which produces a first predetermined airflow profile;
   introducing incremental pressure increases to determine a second pressure, greater than said first critical pressure, which produces a second predetermined airflow profile; and
   setting pressure in said upper airway system using said second pressure.

2. Method according to claim 1, wherein said step of determining further includes the steps of:
   establishing a predetermined airflow limit from at least said roundness feature, said flatness feature and a peak airflow signal, said predetermined airflow limit being adjusted in accordance with predetermined limit modifiers.

3. Method according to claim 2, wherein said first and second predetermined airflow profiles correspond to peak airflow limits when said roundness and flatness features have not changed by more than a predetermined amount.

4. Method according to claim 1, wherein said step of identifying test periods further includes the step of:
   initiating a test period when respiratory instabilities have been detected for a predetermined number of inspiration and expiration periods.

5. Method according to claim 1, wherein said step of determining the non-respiratory component further includes the step of:
   detecting airflow leaks in an airflow path connected with said upper airway system.

6. Method according to claim 1, wherein said step of determining a critical pressure further includes the steps of:
   reducing pressure in said upper airway system by a first predetermined amount; and incrementally reducing pressure in said upper airway system by a second predetermined amount less than said first predetermined amount.

7. Method according to claim 1, further including the step of:

storing extracted features and incremental pressure adjustments in memory.

8. Method according to claim 1 further comprising the step of:

incorporating an additional external input from an oxygen saturation monitor or a snoring monitor.

9. Method according to claim 1 further comprising the step of:

incorporating an additional external input from a monitor of pressure, sound, oxygen saturation or body position.

10. Method for adaptively providing continuous positive airway pressure in an upper airway system comprising the steps of:

detecting airflow in the upper airway system;

averaging said airflow information over a predetermined period of time;

determining respiratory and non-respiratory components of said airflow using said averaged information;

identifying periods of inspiration and expiration using said non-respiratory flow information; and incrementally adjusting pressure in said upper airway system in response to airflow information detected during said period of inspiration.

11. Method according to claim 10, wherein said step of adjusting further includes steps of:

identifying a critical pressure at which a significant obstruction occurs during said inspiration; and identifying an optimum pressure for eliminating said obstruction during said inspiration.

12. Method according to claim 11, wherein said step of identifying a critical pressure and an optimum pressure further includes the step of:

introducing incremental pressure perturbations into said upper airway system;

extracting characteristic features of said upper airway system during inspiration;

using said extracted characteristics to identify the optimum pressure and the critical pressure.

13. Method according to claim 10, wherein said step of adjusting is performed by identifying relative changes in airflow during said step of detecting.

14. Method according to claim 10, wherein said step of adjusting further includes steps of:

extracting features indicative of airflow resistance in said upper airway system.

15. System for providing continuous positive airway pressure in an upper airway system comprising:

means for detecting airflow in an upper airway system of a patient;

means for generating pressure in said upper airway system in response to a command pressure;

means for adaptively controlling said pressure generating means in response to said detecting means to automatically provide continuous positive airway pressure, said adaptive control means introducing incremental pressure perturbations for setting a command pressure relative to a predetermined critical pressure, means for averaging airflow information over a predetermined period of time and for determining non-respiratory flow using said averaged information; and means for identifying periods of inspiration and expiration using said non-respiratory flow information.

16. System according to claim 15, wherein said adaptive control means identifies said critical pressure as a pressure at which a predetermined upper airway obstruction occurs during said inspiration.

17. System according to claim 16, wherein said adaptive control means extracts features indicative of airflow resistance in said upper airway system to identify said critical pressure and to set said command pressure.

18. System according to claim 16, wherein said extracted features include flatness, roundness and peak flow.

* * * * *